(12) United States Patent
Akiyama et al.

(10) Patent No.: US 9,522,199 B2
(45) Date of Patent: Dec. 20, 2016

(54) METHOD FOR COLLECTING METAL-CONTAINING FULLERENE

(75) Inventors: Kazuhiko Akiyama, Hachioji (JP);
Tatsuyuki Hamano, Hachioji (JP);
Hisanori Shinohara, Nagoya (JP);
Yusuke Nakanishi, Nagoya (JP)

(73) Assignee: NATIONAL UNIVERSITY CORPORATION NAGOYA UNIVERSITY, Nagoya-shi (JP)

( * ) Notice: Subject to any disclaimer, the term of this patent is extended or adjusted under 35 U.S.C. 154(b) by 145 days.

(21) Appl. No.: 14/380,815

(22) PCT Filed: Sep. 4, 2012

(86) PCT No.: PCT/JP2012/005589
§ 371 (c)(1),
(2), (4) Date: Nov. 21, 2014

(87) PCT Pub. No.: WO2013/132548
PCT Pub. Date: Sep. 12, 2013

(65) Prior Publication Data
US 2015/0246147 A1  Sep. 3, 2015

(30) Foreign Application Priority Data

Mar. 5, 2012 (JP) ................................. 2012-047496

(51) Int. Cl.
| | | |
|---|---|---|
| A61K 51/12 | (2006.01) | |
| A61K 49/18 | (2006.01) | |
| C01B 31/02 | (2006.01) | |
| B82Y 30/00 | (2011.01) | |
| B82Y 40/00 | (2011.01) | |
| H01B 1/04 | (2006.01) | |

(52) U.S. Cl.
CPC ......... *A61K 51/1268* (2013.01); *A61K 49/189* (2013.01); *B82Y 30/00* (2013.01); *B82Y 40/00* (2013.01); *C01B 31/0213* (2013.01); *H01B 1/04* (2013.01); *Y10S 977/736* (2013.01); *Y10S 977/845* (2013.01)

(58) Field of Classification Search
CPC ......... A16K 49/18; A61K 51/12; A61K 48/00
See application file for complete search history.

(56) References Cited

FOREIGN PATENT DOCUMENTS

| JP | 2000-159514 A | 6/2000 |
| JP | 2005-504700 A | 2/2005 |

OTHER PUBLICATIONS

George A. Olah et al., Convenient separation of high-purity C60 from crude fullerence extract by selective complexation with AlCl3, Proc. Natl. Acad. Sci, USA, vol. 91, 9019-9021, 1994.*
Takayuki Hamano et al., Improvement of Metallofullerene Separation Using Lewis Acid, Japan Society of Nuclear and Radiochemical Sciences, Sep. 20, 2011.*
International Search Report issued Oct. 23, 2012 in PCT/JP2012/005589.
Steven Stevenson, et al., "Selective complexation and reactivity of metallic nitride and oxometallic fullerenes with Lewis acids and use as an effective purification method", Inorganic Chemistry, vol. 48, No. 24, 2009, pp. 11685-11690.
Imre Bucsi, et al., "Convenient separation of high-purity $C_\alpha$ from crude fullerene extract by selective complexation with $AlCl_3$", Proc. Natl. Acad. Sci. USA, vol. 91, Sep. 1994, pp. 9019-9021.
T. Hamano, et al, "Improvement of metallofullerene separation using Lewis acid", Journal of Nuclear and Radiochemical Sciences, A Supplement to vol. 12, Sep. 20, 2011, p. 127 and Cover Page (with English language translation).
Tatsuyuki Hamano, et al., "Improvement of metallofullerene separation using Lewis acid", Fullerene Nanotube Graphene Sogo Symposium Koen Yoshishu, vol. 41, Sep. 5, 2011, p. 120 and Cover Page.
Tatsuyuki Hamano, "Studies on metallofullerene separation using Lewis acid", Abstracts for Master's Thesis Presentation in Academic 2011, Feb. 2012, 2 pages and Cover Page (with English language translation).

* cited by examiner

*Primary Examiner* — Michael G Hartley
*Assistant Examiner* — Jagadishwar Samala
(74) *Attorney, Agent, or Firm* — Oblon, McClelland, Maier & Neustadt, L.L.P.

(57) ABSTRACT

A method for recovering an endohedral metallofullerene comprises a complexation step of adding a Lewis acid comprising titanium halide or tin halide to a reaction solution formed by dissolving crude fullerenes in a solvent, thereby forming a complex of the endohedral metallofullerene and the Lewis acid, a filtering step of filtering the reaction solution to separate the complex, and a washing step of removing the Lewis acid from the complex to obtain the endohedral metallofullerene. The obtained endohedral metallofullerene is soluble in a solvent. This method provides a high recovery yield of the endohedral metallofullerene.

18 Claims, 10 Drawing Sheets

Extract Solution (1)

Fig. 3

Filtrate (2)

METHOD FOR COLLECTING METAL-CONTAINING FULLERENE

TECHNICAL FIELD

The present invention relates to a method for recovering an endohedral metallofullerene.

BACKGROUND ART

Endohedral metallofullerenes are materials which have metal atoms inside their fullerene cages. With electron transfer from the metal atoms to the fullerenes, the endohedral metallofullerenes change in electric properties and electron transport properties of the fullerenes. Therefore, it is believed that the endohedral metallofullerenes can be used in a wide variety of fields such as a medical field and an electronic equipment field. Studies are underway to use, for example, a gadolinium-encapsulated endohedral metallofullerene ($Gd@C_{82}$) in contrast dyes for nuclear magnetic resonance imaging (MRI), a lutetium-encapsulated endohedral metallofullerene ($Lu_3N@C_{80}$) in beta-ray emitting therapeutic agents, a lithium-encapsulated endohedral metallofullerene ($Li@C_{60}$) in n-type semiconductors, and a terbium-encapsulated endohedral metallofullerene ($Tb@C_{82}$) in single-molecule nanodevices.

A method for producing an endohedral metallofullerene comprises forming endohedral metallofullerene-containing soot by arc discharge or the like using, as a raw material, a composite rod prepared by mixing graphite powder and metal oxide powder, as disclosed in Japanese Unexamined Patent Application Publication No. 2000-159,514 (PTL 1).

The endohedral metallofullerene-containing soot contains about 0.1% of an endohedral metallofullerene. Accordingly, the endohedral metallofullerene has been isolated from the endohedral metallofullerene-containing soot by high-performance liquid chromatography (HPLC).

In the method for separating the endohedral metallofullerene by the HPLC, however, about half of the endohedral metallofullerene is adsorbed by a stationary phase in a column. Therefore, loss of the endohedral metallofullerene is large. If all the endohedral metallofullerene adsorbed by the stationary phase is to be recovered, a developing solvent must be passed through the column a lot of times. Accordingly, efficiency in recovering the endohedral metallofullerene is low. Life cycle of the column is relatively short and the column needs to be regularly replaced with a new one.

Moreover, the HPLC needs a large amount of a developing solvent, and it takes a long time to separate an endohedral metallofullerene by the HPLC. For example, separation of 10 mg of an endohedral metallofullerene by the HPLC takes a duration of 1 to 2 months or more. Endohedral metallofullerenes which encapsulate short-half-life elements or unstable substances need to be separated especially rapidly. Besides, the HPLC for separating an endohedral metallofullerene requires a special kind of column, hardware, etc.

Under these circumstances, Steven Stevenson et al (NPL 1) succeeded in extracting $Sc_3N@C_{78}$ and $Sc_4O_2@C_{80}$ by causing a fullerene solution which contains $Sc_3N@C_{78}$, $Sc_4O_2@C_{80}$, etc. to selectively react with $AlCl_3$ or $FeCl_3$ and precipitate. However, the method of Steven Stevenson et al does not attain a sufficiently high recovery yield of endohedral metallofullerenes.

Furthermore, Imre Busci et al (NPL 2) reported that when fullerenes $C_{60}$ and $C_{70}$ are reacted with $AlCl_3$, highly reactive $C_{70}$ forms a complex and $C_{60}$ is separated. However, it takes 2 to 6 days to cause a reaction by the method of Imre Busci et al. Therefore, even if the method of Imre Busci et al is applied to separation of an endohedral metallofullerene, it cannot be expected to separate the endohedral metallofullerene in a short time.

On the other hand, Japanese Unexamined Patent Application Publication (Translation of PCT Application) No. 2005-504,700 (PTL 2) discloses a method comprising forming stable fullerene cations in a solvent from one fullerene group selected from a first fullerene group and a second fullerene group in a fullerene mixture and thereby separating the one fullerene group from the other fullerene group.

CITATION LIST

Patent Literature

[PTL 1] Japanese Unexamined Patent Application Publication No. 2000-159,514
[PTL 2] Japanese Unexamined Patent Application Publication (Translation of PCT Application) No. 2005-504,700

Non-Patent Literature

[NPL 1] Steven Stevenson, etc., Inorg. Chem. 2009, 48, 11685-11690
[NPL 2] Imre Bucsi, etc., Proc. Natl. Acad. Sci. USA, vol. 91, 9012-9021 (1994)

SUMMARY OF INVENTION

Technical Problem

The present inventors have further studied and developed a novel method of recovering an endohedral metallofullerene at a high recovery yield.

The present invention has been made in view of these circumstances, and it is an object of the present invention to provide a method for recovering an endohedral metallofullerene at a high recovery yield.

Solution to Problem

A method for recovering an endohedral metallofullerene, which encapsulates metal, from crude fullerenes, according to the present invention comprises
a complexation step of adding a Lewis acid comprising titanium halide or tin halide to a reaction solution formed by dissolving the crude fullerenes in a solvent, thereby forming a complex of the endohedral metallofullerene and the Lewis acid;
a filtering step of filtering the reaction solution to separate the complex; and
a washing step of removing the Lewis acid from the complex to obtain the endohedral metallofullerene.

Advantageous Effect of Invention

In the method for recovering an endohedral metallofullerene according to the present invention, a liquid-phase Lewis acid comprising titanium halide or tin halide is added to a reaction solution formed by dissolving crude fullerenes containing the endohedral metallofullerene in a solvent so as to cause the endohedral metallofullerene and the Lewis acid to react with each other and form residue comprising a complex of the endohedral metallofullerene and the Lewis acid. Accordingly, the endohedral metallofullerene can be recovered at a high recovery yield.

DESCRIPTION OF THE INVENTION

Figure 1:
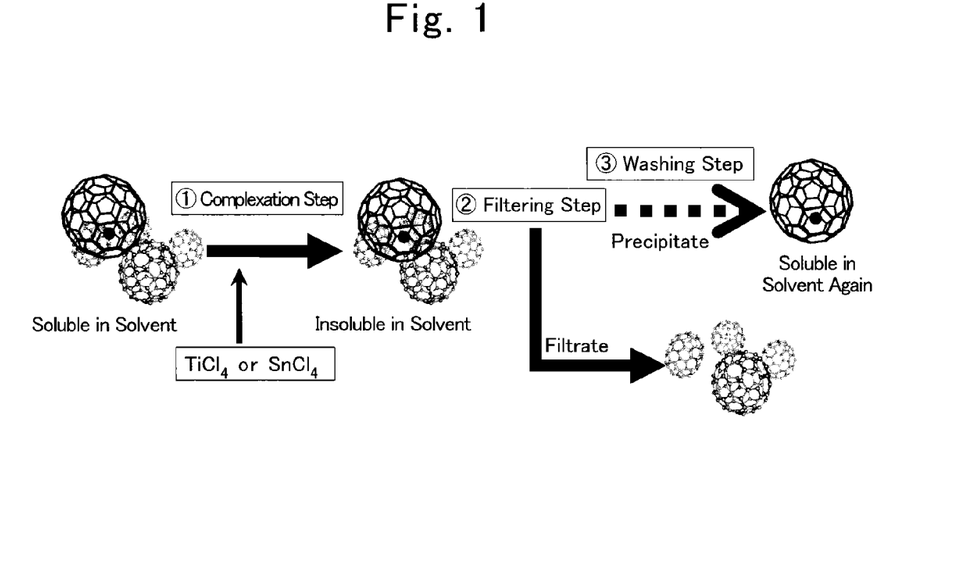
FIG. 1 is an explanatory view illustrating a principle of the method for recovering an endohedral metallofullerene according to the present invention.

A method for recovering an endohedral metallofullerene according to an embodiment of the present invention will be described. The method for recovering an endohedral metallofullerene according to the present embodiment is a method for recovering an endohedral metallofullerene from crude fullerenes. In order to recover the endohedral metallofullerene from the crude fullerenes, a complexation step, a filtering step, a washing step, and a dissolving step are performed. As shown in FIG. 1, in the complexation step, a predetermined kind of Lewis acid is added to a reaction solution formed by dissolving crude fullerenes comprising an endohedral metallofullerene and an unencapsulated fullerene in a solvent, so as to form a complex of the endohedral metallofullerene and the Lewis acid. In the filtering step, the complex was filtered to separate residue from a filtrate. In the washing step, the residue is washed with water or the like. A dissolving step for dissolving the endohedral metallofullerene in a solvent can be performed after the washing step. Hereinafter, the crude fullerenes and each of the steps will be described in detail.

Crude Fullerenes

Crude fullerenes are a variety of materials having fullerene shells, and include one or more endohedral metallofullerenes, which encapsulate metal in their fullerene shells. The crude fullerenes include at least one endohedral metallofullerene. In addition to the endohedral metallofullerene, the crude fullerenes may include an unencapsulated fullerene which encapsulates no metal. The unencapsulated fullerene which encapsulates no metal includes not only an empty-cage fullerene, which encapsulates nothing, but also a non-metal-encapsulated fullerene, which does not encapsulate any metal element but encapsulates a non-metal element. The method for recovering an endohedral metallofullerene according to the present invention can be applied to a method for separating an endohedral metallofullerene from crude fullerenes by using crude fullerenes which include, for example, the endohedral metallofullerene and an unencapsulated fullerene which encapsulates no metal and performing the complexation step, the filtering step and the washing step. The method according to the present invention can also be applied to a method for replacing a solvent of an endohedral metallofullerene. The method for recovering an endohedral metallofullerene according to the present invention can also be applied to methods other than the above.

The endohedral metallofullerene can encapsulate a variety of metals. Metals to be easily encapsulated in fullerenes include elements in groups 1A, 2A, 3A, and 4A of the periodic table. Examples of the metals to be easily encapsulated in fullerenes include Li (lithium), Na (sodium), K (potassium), Rb (rubidium), Cs (cesium), Fr (francium), Be (beryllium), Mg (magnesium), Ca (calcium), Sr (strontium), Ba (barium), Ra (radium), Sc (scandium), Y (yttrium), lanthanides, and actinides. Among them, Li, Ca, Sr, Ba, Sc, Y, Ti, Zr, and Hf are preferred. In the lanthanides, La (lanthanum), Ce (cerium), Pr (praseodymium), Nd (neodymium), Sm (samarium), Eu (europium), Gd (gadolinium), Tb (terbium), Dy (dysprosium), Ho (holmium), Er (erbium), Tm (thulium), Yb (ytterbium), Lu (lutetium) are preferred. In the actinides, Ac (actinium), Th (thorium), Pa (protactinium), U (uranium), Np (neptunium), Pu (plutonium), and Am (americium) are preferred.

The endohedral metallofullerene can contain a non-metal element. Examples of the non-metal element which can be encapsulated together with metal include hydrogen, carbon, nitrogen, oxygen and sulfur.

Fullerenes which easily encapsulate metal are higher fullerenes having large sizes (for example, having 70 or more carbon atoms). The presence ratio of higher fullerenes in crude fullerenes is small. Accordingly, the presence ratio of endohedral metallofullerenes, i.e., metal-encapsulated higher fullerenes in crude fullerenes is about several percent.

A fullerene has a polyhedral structure formed by a plurality of carbon atoms. The fullerene has a space portion on an inside thereof, and can encapsulate a variety of metals in the space portion. Preferably fullerenes capable of encapsulating metal are fullerenes having 60 to 200 carbon atoms and more preferably fullerenes having 60 to 96 carbon atoms. Such a fullerene can encapsulate one or more metal elements.

The method for recovering an endohedral metallofullerene according to the present invention can recover an endohedral metallofullerene which encapsulates one or more of such a variety of metals as mentioned above at a high recovery yield.

The crude fullerenes can be produced by any method but it is preferred that the crude fullerenes are, for example, extracted from soot formed by applying heat treatment to a composite rod of carbon and metal. The crude fullerenes can also be prepared by an ion implantation method.

Soot is formed by applying heat treatment to a composite rod of carbon and metal. Preferably the composite rod is formed by applying heat treatment to a mixture of carbon and metal at a high temperature (e.g., 1,600 to 2,000 deg. C.). The composite rod can be a commercially available one. Examples of the heat treatment to the composite rod include arc discharge and laser evaporation.

The soot formed by applying heat treatment to the composite rod contains crude fullerenes at a ratio of about 10 to 20%. The soot contains amorphous carbon such as open-cage fullerenes and graphene in addition to the crude fullerenes.

The soot contains components other than the crude fullerenes. Accordingly, it is necessary to extract the crude fullerenes from the soot. In order to extract the crude fullerenes from the soot, a solvent is added to the soot to dissolve the crude fullerenes in the soot. A solution prepared by adding the solvent to the soot is filtered with a filter body such as a membrane.

The solvent to be added to the soot is a liquid capable of dissolving the crude fullerenes. Preferably the solvent to be added to the soot is a solvent which can be used as a solvent in a reaction solution for a complexation reaction with a Lewis acid. Preferred examples of such a solvent include $CS_2$ and benzene-based solvents. Preferred examples of the benzene-based solvents include toluene, o-dichlorobenzene, 1,2,4-trichlorobenzene, and o-xylene. Left on the filter body as residue is a component which is not dissolved in the solvent (e.g., amorphous carbon), and a filtrate contains crude fullerenes which are dissolved in the solvent. The amount of the solvent added to 1 g of the soot is preferably not more than 50 ml, and more preferably 20 to 30 ml. When the amount of the solvent is too small, the amount of the crude fullerenes extracted from the soot may decrease. When the amount of the solvent is too large, it means that the solvent is used in an amount more than necessary to extract the crude fullerenes, that is to say, the solvent is wasted.

Complexation Step

In the complexation step, a Lewis acid comprising titanium halide or tin halide is added to a reaction solution containing the crude fullerenes, thereby forming a complex of an endohedral metallofullerene and the Lewis acid.

A Lewis acid comprising at least one selected from the group consisting of titanium halide and tin halide is added to a reaction solution comprising the crude fullerenes and a solvent. This addition yields a precipitate comprising a complex of an endohedral metallofullerene and the Lewis acid. There is a general tendency that metal in a fullerene is positively charged and the fullerene is negatively charged. Therefore, it is believed that the Lewis acid is attracted by the fullerene and forms a complex of an endohedral metallofullerene and the Lewis acid. The complex of the endohedral metallofullerene and the Lewis acid is not soluble in the solvent and precipitates in the reaction solution. On the other hand, an unencapsulated fullerene which encapsulates no metal is not electrically charged. Therefore, the Lewis acid is not attracted by the unencapsulated fullerene. Therefore, the unencapsulated fullerene keeps dissolved in the reaction solution.

The method for recovering an endohedral metallofullerene according to the present invention can separate an endohedral metallofullerene at a high recovery yield despite fullerene size, the kind of encapsulated metal, valence of encapsulated metal, and the number of encapsulated metal atoms. Moreover, even when an endohedral metallofullerene encapsulates a non-metal element together with a metal element, the method according to the present invention can separate the endohedral metallofullerene at a high recovery yield.

Preferably the complex of the endohedral metallofullerene and the Lewis acid is constituted by one molecule of endohedral metallofullerene and a plurality of molecules of the Lewis acid. As will be discussed later in the description of experiments, it is preferred that a plurality of molecules of the Lewis acid surround one molecule of the endohedral metallofullerene. Preferably 5 to 30 molecules, more preferably 10 to 20 molecules of the Lewis acid surround one molecule of the endohedral metallofullerene.

The Lewis acid is at least one selected from the group consisting of titanium halide and tin halide. Both titanium halide and tin halide easily form a complex with an endohedral metallofullerene. As will be clear from the experiments mentioned later, each of titanium halide and tin halide more easily forms a complex with an endohedral metallofullerene than other Lewis acids, so the recovery yield of the endohedral metallofullerene is high.

Examples of titanium halide used as a Lewis acid in the complexation step include $TiF_4$, $TiCl_4$, $TiBr_4$, and $TiI_4$. $TiCl_4$ is especially preferred. Examples of tin halide used as a Lewis acid in the complexation step include $SnF_4$, $SnCl_4$, $SnBr_4$, and $SnI_4$. $SnCl_4$ is especially preferred. Since $TiCl_4$ and $SnCl_4$ are highly reactive Lewis acids and have the liquid phase at room temperature, $TiCl_4$ and $SnCl_4$ can rapidly contact an endohedral metallofullerene and forms a complex. Therefore, the endohedral metallofullerene can be separated at a high recovery yield.

When the crude fullerenes are extracted from soot formed by applying heat treatment to a composite rod of carbon and metal, the crude fullerenes often contain not only an endohedral metallofullerene but also an unencapsulated fullerene which encapsulates no metal. In this case, the amount of a Lewis acid added to 1 mg of the crude fullerenes in a reaction solution is preferably 0.3 to 30 mg, more preferably 0.5 to 15 mg, and desirably 1 to 12 mg. When the amount of the Lewis acid added is too small, a complex of the endohedral metallofullerene and the Lewis acid is difficult to be formed, and a recovery yield of the endohedral metallofullerene may decrease. When the amount of the Lewis acid added is too large, it means that the Lewis acid is used in an amount more than necessary, that is to say, the Lewis acid is wasted.

When almost 100% of crude fullerenes is constituted by an endohedral metallofullerene, almost 100% of the crude fullerenes make a complexation reaction with a Lewis acid.

Therefore, preferably the amount of the Lewis acid added to the crude fullerenes in a reaction solution is greater than the amount of the Lewis acid added to the abovementioned crude fullerenes extracted from the soot. For example, the amount of the Lewis acid added to 1 mg of the crude fullerenes in a reaction solution is preferably 6 to 1,000 mg, more preferably 14 to 300 mg, and desirably 20 to 120 mg. When the amount of the Lewis acid added is too small, a complex of the endohedral metallofullerene and the Lewis acid is difficult to be formed and the recovery yield of the endohedral metallofullerene may decrease. When the amount of the Lewis acid added is too large, it means that the Lewis acid is used in an amount more than necessary, that is to say, the Lewis acid is wasted.

In each of the case where crude fullerenes are extracted from the soot and the case where almost 100% of crude fullerenes is constituted by an endohedral metallofullerene, the amount of the Lewis acid added to 1 ml of a reaction solution is preferably 3 to 100 mg, more preferably 7 to 15 mg, and desirably 10 to 12 mg.

When a Lewis acid is added to a reaction solution, a complexation reaction occurs between an endohedral metallofullerene and the Lewis acid. Shorter time for the complexation reaction is better. Preferably time for the complexation reaction is not less than 0.2 second and less than 1 hour. If the reaction time is shorter than 0.2 second, a sufficiently large amount of the complex may not be formed. If the reaction time is 24 hours or longer, molecules of the endohedral metallofullerene may react with each other to form a polymer, and the rate of forming a complex of the endohedral metallofullerene and the Lewis acid may decrease. Therefore, the recovery yield of the endohedral metallofullerene may decrease. Furthermore, desirably the reaction time falls within a range of 1 second to 12 hours, and more desirably within a range of 5 seconds to 1 hour. In these cases, a complex is formed at a high rate and accordingly the recovery yield of an endohedral metallofullerene further improves.

Preferably temperature at the reaction is room temperature. Preferably the reaction is performed in a dry atmosphere in order to prevent a decrease in activity of the Lewis acid and generation of an acid gas. Moreover, the reaction can be performed in the air as long as caution is taken not to breathe an acid gas, etc.

Filtering Step

A filtering step is performed after the complexation step. In the filtering step, the reaction solution after the reaction is filtered to separate the complex of the endohedral metallofullerene and the Lewis acid. The reaction solution after the reaction contains residue containing the complex of the endohedral metallofullerene and the Lewis acid. Upon filtering the reaction solution after the reaction to separate the residue, the reaction between the endohedral metallofullerene and the Lewis acid stops. The residue obtained by filtering comprises the complex of the endohedral metallofullerene and the Lewis acid.

A method for filtering the reaction solution to separate the complex of the endohedral metallofullerene and the Lewis acid uses a membrane, for instance. Preferably micropores of the membrane have a size which is smaller than that of the complex and greater than that of the fullerene. In general, the size of the micropores of the membrane is preferably 0.20 to 0.45 μm, although depending on the size of the complex or the fullerene.

Washing Step

A washing step is performed after the filtering step. In the washing step, the complex is washed to remove the Lewis acid from the complex. With this step, the endohedral metallofullerene is refined. In order to remove the Lewis acid from the complex, a washing solution capable of eluting the Lewis acid from the complex is used. Preferably water or aqueous solutions of weak-acid salts are used as a washing solution. Among them, water is preferred.

A method for washing the residue comprises, for example, causing a washing solution to flow down onto the residue comprising the complex left on the membrane. The Lewis acid in the residue flows down together with the washing solution. The endohedral metallofullerene is left on the membrane. Preferably the amount of the washing solution used with respect to 1 mg of the endohedral metallofullerene falls within a range of 2 to 10 ml and desirably within a range of 3 to 5 ml. When the amount of the washing solution is too small, the Lewis acid forming a complex with the endohedral metallofullerene may be left in the residue, and the recovery yield of the endohedral metallofullerene may decrease. Since the washing solution hardly mixes with a solvent capable of dissolving the endohedral metallofullerene, when the amount of the washing solution is too large, the washing solution may be left in the residue and make it difficult for the endohedral fullerene to be dissolved in the solvent capable of dissolving the endohedral fullerene.

Dissolving Step

A dissolving step may be performed after the washing step. In the dissolving step, the solvent which dissolved the crude fullerenes before the complexation step can be replaced with a different solvent, and unlike an ordinary solvent replacing method using heat treatment, solvent replacement can be performed without any heat treatment. Therefore, the method for recovering an endohedral metallofullerene according to the present invention is also effective as a solvent replacing method for a thermally unstable endohedral metallofullerene. In the dissolving step, of course, the endohedral metallofullerene can be dissolved again in the same solvent as the solvent which dissolved the crude fullerenes before the complexation step. Moreover, when the crude fullerenes contain an unencapsulated fullerene in addition to the endohedral metallofullerene, it is useful to dissolve the endohedral metallofullerene obtained in the washing step again in a solvent in the present method for separating the endohedral metallofullerene from the crude fullerenes.

In the dissolving step, the endohedral metallofullerene from which the Lewis acid was removed is obtained by dissolving the endohedral metallofullerene again in a solvent. Preferably the solvent to dissolve the endohedral metallofullerene again is $CS_2$ or benzene-based solvents. Among them, $CS_2$ and 1,2,4-trichlorobenzene are preferred. A method for dissolving the endohedral metallofullerene again in a solvent comprises, for example, causing the solvent to flow down on the endohedral metallofullerene left on the membrane. Any solvent can be employed as long as it can dissolve the endohedral metallofullerene, and $CS_2$ and benzene-based solvents are most preferred. Thus, the endohedral metallofullerene is obtained. Preferably, the amount of the solvent added to 1 mg of the endohedral metallofullerene falls within a range of 0.1 to 10 ml and more desirably within a range of 1 to 5 ml. When the amount of the solvent is too small, the solvent cannot sufficiently dissolve the endohedral metallofullerene and the recovery yield of the endohedral metallofullerene may decrease. On the other hand, when the amount of the solvent is too large, it means that the solvent is used in an amount more than necessary, that is to say, the solvent is wasted.

EXAMPLE

Example 1

In the present example, gadolinium-encapsulated fullerene was separated from crude fullerenes which were extracted from soot.

Composite rods (trade name Klasta Mate, produced by Toyo Tanso Co., Ltd.) of carbon and gadolinium (Gd) were prepared. The composite rods were formed by applying heat treatment to a mixture of 90.4 mass % of graphite powder and 9.6 mass % of Gd powder. As a pretreatment, the composite rods were baked at a current value of 320 A (ampere) for 30 minutes.

Arc discharge was performed using the pretreated composite rods and arc discharge apparatus. The arc discharge apparatus was MS20/15MA (produced by Ulvac Material Co., Ltd., currently known as Ulvac, Inc.) and had a cathode block and an anode holder for holding a composite rod to serve as an anode block in a discharge chamber. The cathode block and the anode block have a gap of 1 to 2 mm and an arc discharge was generated therebetween. Discharge current was 500 A and discharge voltage was 28 to 32 V, and the number of polarity conversion times was 8. The chamber during arc discharge has an anaerobic atmosphere comprising 7.7 to 7.8 kPa of the air and 1.6 kPa of helium. Discharge time was 110 minutes. When the abovementioned arc discharge was carried out using 105.4 g of the composite rods, soot was formed in the chamber. Then, 50.3 g of the soot was collected. $CS_2$ was added to the soot and the mixture was stirred and filtered by a membrane having a pore size of 0.45 μm. A component insoluble in the solvent was left as residue on the membrane and crude fullerenes were dissolved in an extract solution (a filtrate) which passed through the membrane. 10 mg of crude fullerenes were dissolved in 1 ml of the extract solution.

In a complexation step, the abovementioned extract solution which passed through the membrane was used as a reaction solution, and added with a Lewis acid $TiCl_4$ and stirred, thereby causing an endohedral metallofullerene and $TiCl_4$ to react with each other. The reaction was carried out in a dry, inert-gas (argon, nitrogen, etc.) atmosphere in a glove box at room temperature. The amount of $TiCl_4$ added to 1 ml of the reaction solution was 11 mg. The amount of $TiCl_4$ added to 1 mg of the crude fullerenes in the reaction solution was 1.1 mg. Reaction time was 30 seconds. The $CS_2$ solution before the reaction was light brown. As soon as $TiCl_4$ was dropped into the $CS_2$ solution, the reaction started and a precipitate was yielded. When reaction times exceeded 10 minutes, the reaction solution turned yellow.

In a filtering step, the reaction solution was filtered using a filter device. The filter device was a syringe having a filter at a tip. The filter was Millex-LG produced by Millipore Corporation and a membrane having a pore size of 0.20 to 0.45 μm was placed in a fluid passage in the filter. The reaction solution was loaded in the syringe and was passed through the filter. The precipitate as residue was deposited on the membrane in the filter.

In a washing step, water was loaded in the syringe and the residue on the membrane in the filter was washed with water. The amount of the water used with respect to 10 mg of the residue was 5 ml.

In a dissolving step, $CS_2$ was passed through the filter to dissolve the abovementioned residue on the membrane in the filter again. The amount of $CS_2$ added to 1 mg of the residue on the filter was 2 to 6 ml.

The reaction solution (1) in the complexation step, the filtrate (2) in the filtering step, and the residue (3) dissolved again in the solvent in the dissolving step were separated by high-performance liquid chromatography (HPLC). The HPLC conditions were as follows. HPLC apparatus: LC-9104HS produced by Japan Analytical Industry Co., Ltd., Column: Buckyprep produced by Nacalai Tesque, Inc., Mobile phase solvent: toluene, Mobile phase flow rate: 21 ml/min. Since a strong peak was detected in a fraction with a retention time of 32 to 38 minutes in each sample, this fraction was separated and dried into powder. The powder was analyzed by time-of-flight mass spectrometry (TOF-MS). Fullerene size and the number of metal element (Gd) atoms encapsulated in a fullerene were calculated from analytical results of each sample.

Figure 2:
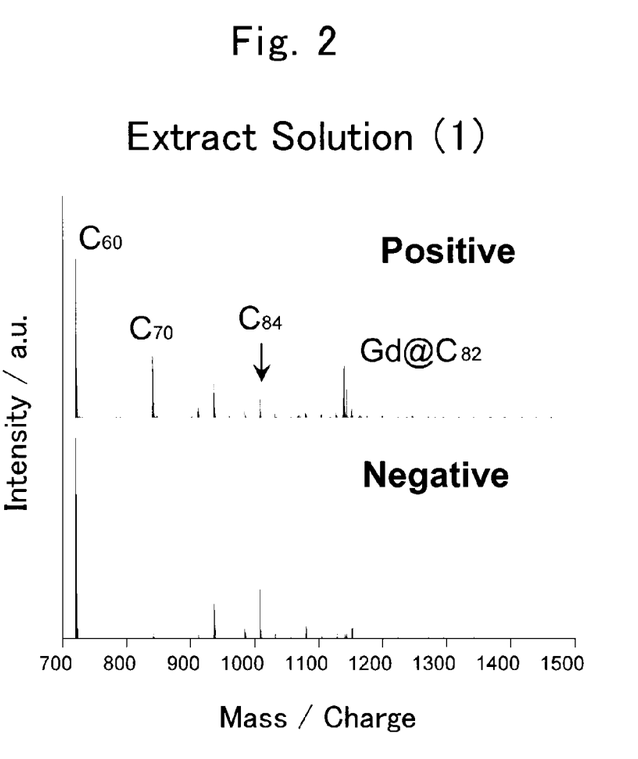
FIG. 2 shows analytical results of fullerenes in a reaction solution (1) of Example 1, and an upper part of FIG. 2 shows a mass spectrum of positive ions of the fullerenes and a lower part of FIG. 2 shows a mass spectrum of negative ions of the fullerenes.
Figure 3:
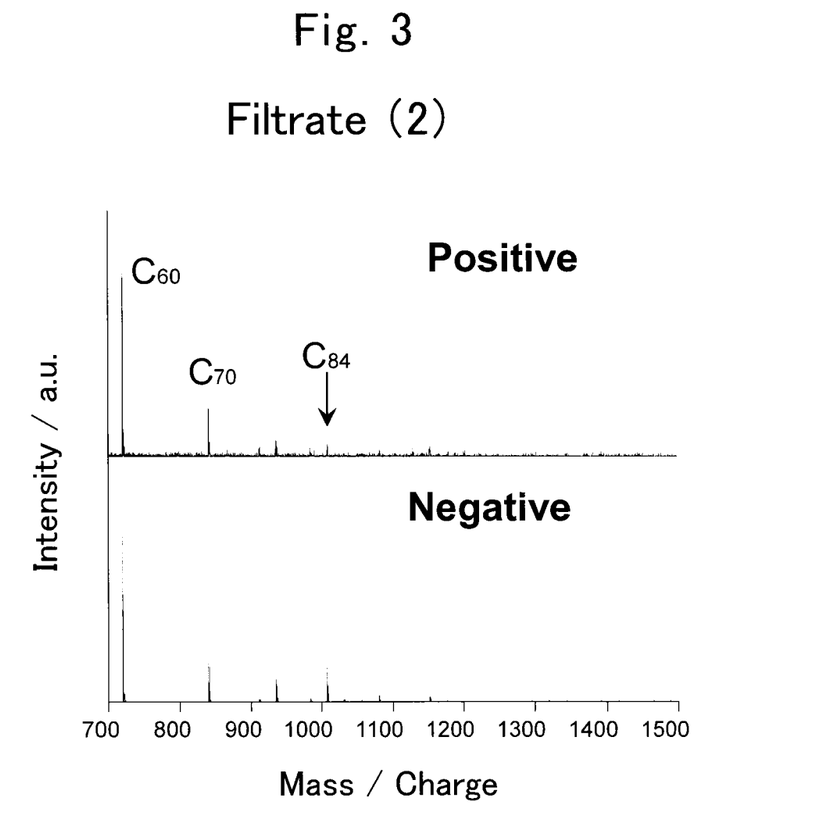
FIG. 3 shows analytical results of fullerenes in a filtrate (2) of Example 1, and an upper part of FIG. 3 shows a mass spectrum of positive ions of the fullerenes and a lower part of FIG. 3 shows a mass spectrum of negative ions of the fullerenes.
Figure 4:
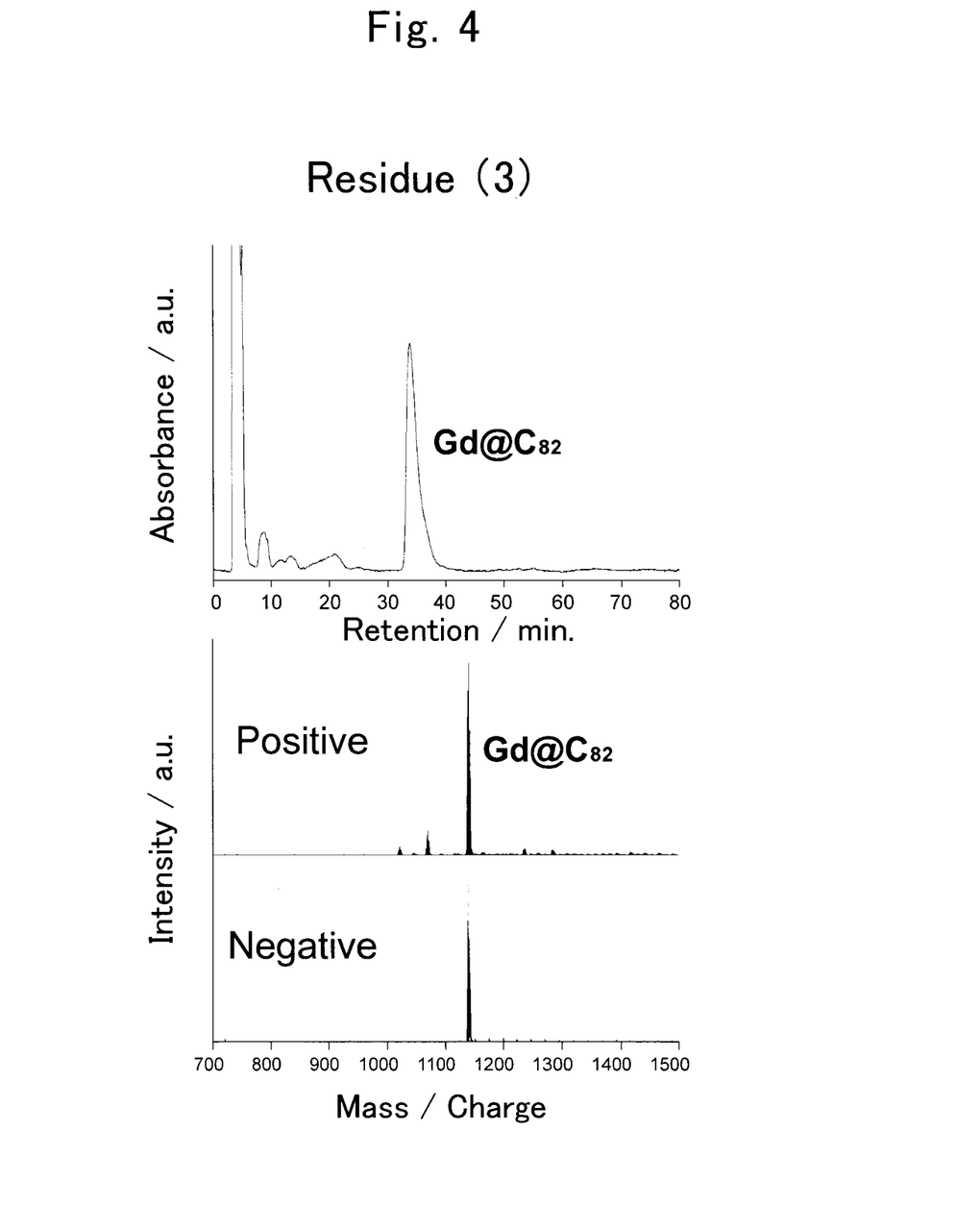
FIG. 4 shows analytical results of fullerenes in residue (3) of Example 1, and an upper part of FIG. 4 shows a chromatogram of HPLC separation of the residue (3), a middle part of FIG. 4 shows a mass spectrum of positive ions of the fullerenes, and a lower part of FIG. 4 shows a mass spectrum of negative ions of the fullerenes.

An analytical result of fullerenes in the reaction solution (1) is shown in FIG. 2, an analytical result of fullerenes in the filtrate (2) is shown in FIG. 3, and an analytical result of fullerenes in the residue (3) is shown in FIG. 4. In each of FIGS. 2 and 3, an upper part shows a mass spectrum of positive ions of the fullerenes and a lower part shows a mass spectrum of negative ions of the fullerenes. In FIG. 4, an upper part shows a chromatogram of HPLC separation of the residue (3), a middle part shows a mass spectrum of positive ions of the fullerenes, and a lower part show a mass spectrum of negative ions of the fullerenes. In the fullerenes of the positive ions, endohedral metallofullerenes tend to be more strongly detected than unencapsulated fullerenes. In the mass spectrum of the fullerenes of the negative ions, unencapsulated fullerenes tend to be more strongly detected than endohedral metallofullerenes. Therefore, first, presence of an endohedral metallofullerene is confirmed by a mass spectrum of positive ions of fullerenes, and then absence of unencapsulated fullerenes is confirmed by a mass spectrum of negative ions of the fullerenes.

In the present description and drawings, an endohedral metallofullerene, which encapsulates a metal element, is expressed by $M@C_n$ (M is a metal element, C is a fullerene, and n is the number of carbon atoms constituting the fullerene). An unendohedral fullerene which encapsulates no metal is expressed by $C_n$ (C is a fullerene and n is the number of carbon atoms constituting the fullerene).

As shown in FIG. 2, in the reaction solution (1) in the complexation step, presence of a fullerene which encapsulates one atom of Gd, $Gd@C82$ was confirmed. Also confirmed were unencapsulated fullerenes which encapsulated no metal and had such a variety of size sizes as $C_{60}$, $C_{70}$, and $C_{84}$.

As shown in FIG. 3, in the filtrate (2), there was not any endohedral fullerene but there were unencapsulated fullerenes of a variety of sizes.

As shown in FIG. 4, in the residue (3), an endohedral metallofullerene $Gd@C_{82}$ was confirmed but unencapsulated fullerenes were not confirmed.

It is seen from the above that an endohedral metallofullerene and unencapsulated fullerenes were present in the extract solution of the soot and, upon causing the endohedral metallofullerene to form a complex with $TiCl_4$ and precipitate, filtering the reaction solution, the unencapsulated fullerenes were contained in the filtrate and the endohedral metallofullerene was left in the residue.

Using the method for recovering an endohedral metallofullerene according to the present invention, 59.9 mg of gadolinium-encapsulated endohedral metallofullerene was recovered with respect to 1.0 g of crude fullerenes. This means that 6.0 mass % of gadolinium-encapsulated endohedral metallofullerene was recovered with respect to 100 mass % of the whole crude fullerenes.

Quantitative analysis of metals (Ti and Gd) in the residue left on the membrane in the filtering step was executed using an inductively coupled plasma mass spectrometer (ICP-MS). As an analytical result, the ratio of Ti to Gd was Ti:Gd=18:1. Since one atom of Gd was encapsulated in each fullerene shell, the ratio of Ti to Gd was equal to the ratio of Ti to the endohedral metallofullerene. It means that 18 molecules of the Lewis acid were present with respect to one molecule of the endohedral metallofullerene.

In the endohedral metallofullerene, since a metal element is positively charged, a fullerene shell is negatively charged. $Ti^{4+}$ of the Lewis acid $TiCl_4$ is attracted by the negatively charged fullerene shell. It is assumed that about 10 to 20 molecules of the Lewis acid surround one molecule of the endohedral metallofullerene.

Example 2

Next, thulium (Tm) was encapsulated in fullerenes and obtained endohedral metallofullerenes were separated in a similar way to that of Example 1.

Composite rods (trade name Klasta Mate, produced by Toyo Tanso Co., Ltd.) of carbon and thulium (Tm) were prepared. The composite rods comprised 89.8 mass % of graphite powder and 10.2 mass % of Tm powder.

Soot was collected by baking the composite rods and then causing arc discharge therebetween in a similar way to that of Example 1 and crude fullerenes were extracted from the soot. Using the crude fullerenes, a complexation step, a filtering step, a washing step and a dissolving step were performed in a similar way to that of Example 1. Solvents used in the steps were $CS_2$ and a Lewis acid used in the complexation step was $TiCl_4$. The amount of $TiCl_4$ added to 1 ml of a reaction solution was 11 mg. The amount of $TiCl_4$ added to 1 ml of the crude fullerenes in the reaction solution was 1.1 mg. Reaction time was 60 seconds.

Figure 5:
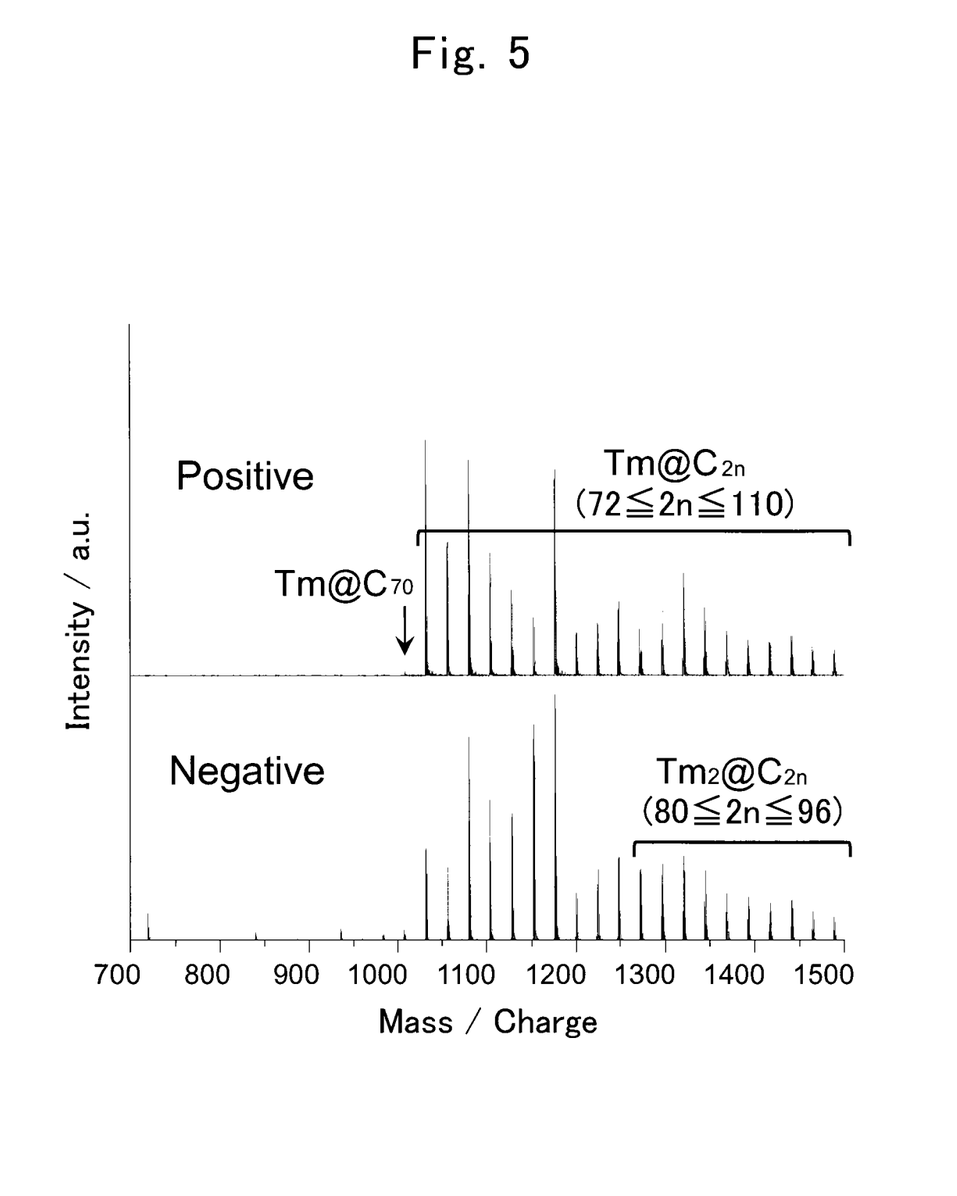
FIG. 5 shows mass spectrometry results of fullerenes in residue (3) of Example 2, and an upper part of FIG. 5 shows a mass spectrum of positive ions of the fullerenes by TOF-MS, and a lower part of FIG. 5 shows a mass spectrum of negative ions of the fullerenes by TOF-MS.

Fullerenes in residue (3) dissolved again in the solvent in the dissolving step was analyzed by HPLC and TOF-MS and analytical results are shown in FIG. 5. In FIG. 5, an upper part shows a mass spectrum of positive ions of the fullerenes and a lower part shows a mass spectrum of negative ions of the fullerenes.

As shown in FIG. 5, endohedral metallofullerenes having a variety of molecular weights were detected. According to estimation of fullerene size and the number of encapsulated metal element atoms from the molecular weight, Tm was encapsulated in fullerenes having carbon atoms of 72 to 110.

Moreover, one or two Tm atoms were encapsulated in one fullerene shell. Each shell of the endohedral metallofullerenes which encapsulated one Tm atom was constituted by carbon atoms of an even number ranging from 72 to 110, inclusive. That is to say, $Tm@C_{2n}$ ($72 \leq 2n \leq 110$) was detected. Besides, each shell of the endohedral metallofullerenes which encapsulated two Tm atoms was constituted by carbon atoms of an even number ranging from 80 to 96, inclusive. That is to say, $Tm_2@C_{2n}$ ($80 \leq 2n \leq 96$) was detected.

When one Tm atom is encapsulated in each shell of the fullerenes, Tm has a valence of 2. On the other hand, when two Tm atoms are encapsulated in each shell of the fullerenes, Tm has a valence of 3.

It is seen from the above that a variety of endohedral metallofullerenes can be recovered at a high recovery yield despite of fullerene size, the number of encapsulated metal element atoms, valence of an encapsulated metal element.

Example 3

In this example, lutetium (Lu)-encapsulated endohedral metallofullerenes were separated in a similar way to that of Example 1.

Composite rods (trade name Klasta Mate, produced by Toyo Tanso Co., Ltd.) of Lu and carbon were prepared. The composite rods comprised 80.8 mass % of graphite powder and 19.2 mass % of Lu powder. Soot was collected by baking the composite rods and then causing arc discharge therebetween and crude fullerenes were extracted from the soot under similar conditions to those of Example 1. Using an extract solution of the crude fullerenes as a reaction solution, a complexation step, a filtering step, a washing step and a dissolving step were performed in a similar way to that of Example 1. A solvent used in the complexation step was $CS_2$ and a Lewis acid used in the complexation step was $TiCl_4$. The amount of $TiCl_4$ added to 1 ml of the reaction solution was 11 mg. The amount of $TiCl_4$ added to 1 mg of the crude fullerenes in the reaction solution was 1.1 mg. Reaction time was 60 seconds.

Figure 6:
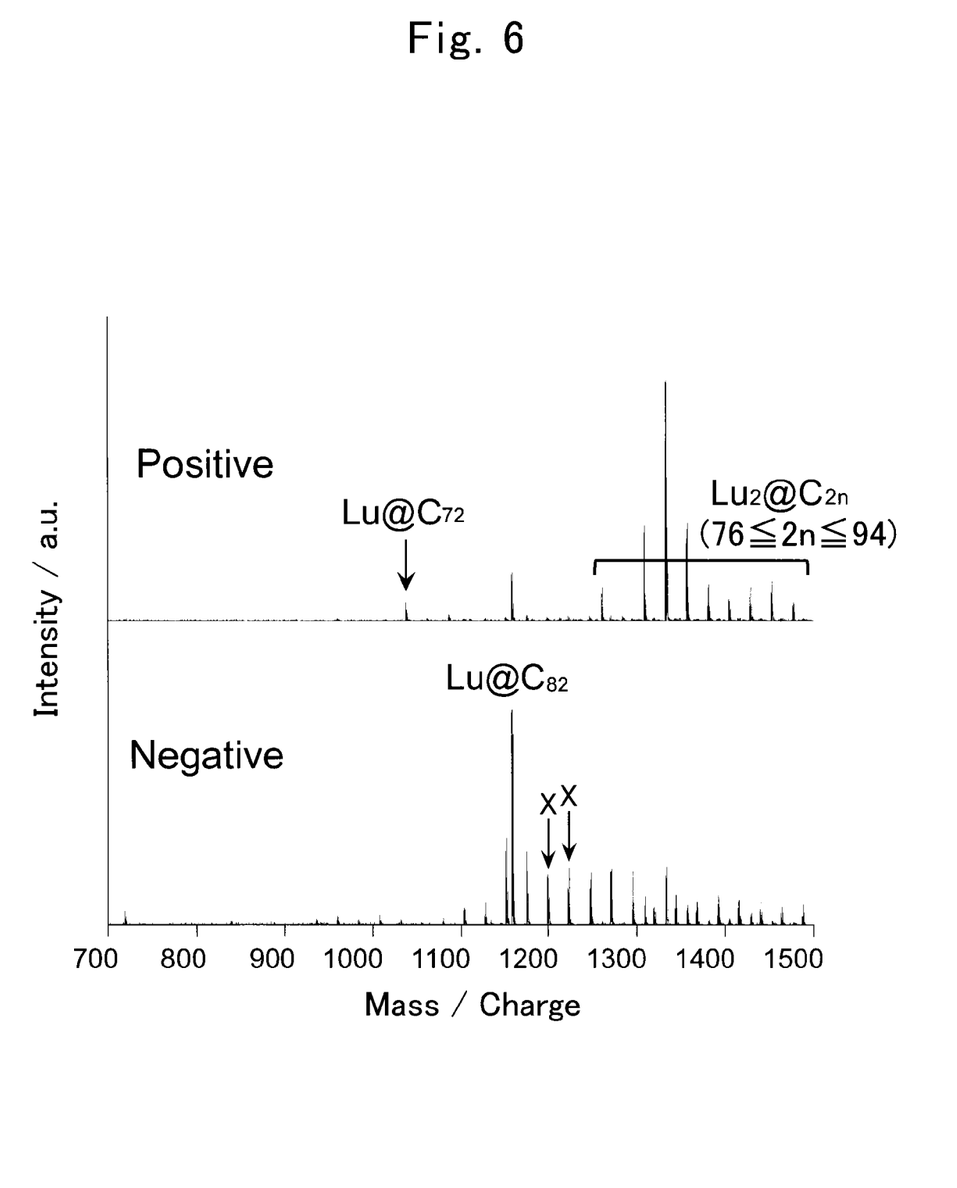
FIG. 6 shows mass spectrometry results of fullerenes in residue (3) of Example 3, and an upper part of FIG. 6 shows a mass spectrum of positive ions of the fullerenes by TOF-MS and a lower part of FIG. 6 shows a mass spectrum of negative ions of the fullerenes by TOF-MS.

Fullerenes in residue (3) dissolved again in a solvent in the dissolving step was analyzed by HPLC separation and TOF-MS, and analytical results are shown in FIG. 6. In FIG. 6, an upper part shows a mass spectrum of positive ions of the fullerenes and a lower part shows a mass spectrum of negative ions of the fullerenes.

As shown in FIG. 6, endohedral metallofullerenes having a variety of molecular weights were detected. According to estimation of fullerene size and the number of encapsulated metal element atoms from the molecular weights, Lu was encapsulated in fullerenes having carbon atoms ranging from 72 to 94, inclusive.

Moreover, one or two Lu atoms were encapsulated in each fullerene shell. Each shell of the endohedral metallofullerenes which encapsulated one Lu atom was constituted by carbon atoms of an even number ranging from 72 to 82, inclusive. That is to say, $Lu@C_{2n}$ ($72 \leq 2n \leq 96$) was detected. Moreover, each shell of the endohedral fullerenes which encapsulated two Lu atoms was constituted by carbon atoms of an even number ranging from 76 to 94, inclusive. That is to say, $Lu_2@C_{2n}$ ($76 \leq 2n \leq 94$) was detected. When one or two Lu atoms were encapsulated in each shell of the fullerenes, Lu has a valence of 3.

It is seen from the above that when an encapsulated metal element is Lu, a variety of endohedral metallofullerenes can be recovered at a high recovery yield despite fullerene size, the number of encapsulated metal element atoms, valence of the encapsulated metal element.

It should be noted that when fullerenes have a molecular weight of 1,100 or more, unencapsulated fullerenes were detected, for example, as indicated by X in FIG. 6, though the amount is very small. Peaks attributed to the unencapsulated fullerenes are two peaks indicated by X in FIG. 6 and peaks repeated at equal intervals to that of the two peaks. This is assumed to be because when fullerenes have larger sizes, the fullerenes have smaller band gaps and accordingly unencapsulated fullerenes more easily interact with $TiCl_4$ in the complexation step.

Example 4

In this example, a lanthanum (La)-encapsulated endohedral metallofullerene was separated in a similar way to that of Example 1.

Composite rods (trade name Klasta Mate, produced by Toyo Tanso Co., Ltd.) of La and carbon were prepared. The composite rods comprised 91.7 mass % of graphite powder and 8.3 mass % of La oxide powder. Soot was collected by baking the composite rods and causing arc discharge therebetween under similar conditions to those of Example 1, and crude fullerenes were extracted from the soot. Using an extract solution of the crude fullerenes as a reaction solution, a method for recovering an endohedral metallofullerene comprising a complexation step, a filtering step, a washing step and a dissolving step was carried out in a similar way to that of Example 1. A solvent in the reaction solution was $CS_2$ (2 ml) and a Lewis acid used was $TiCl_4$ (23.3 mg). The amount of $TiCl_4$ added to 1 ml of the reaction solution was 11.7 mg. The amount of $TiCl_4$ added to 1 mg of the crude fullerenes in the reaction solution was 10 mg. Reaction time was 1 minute.

Figure 7:
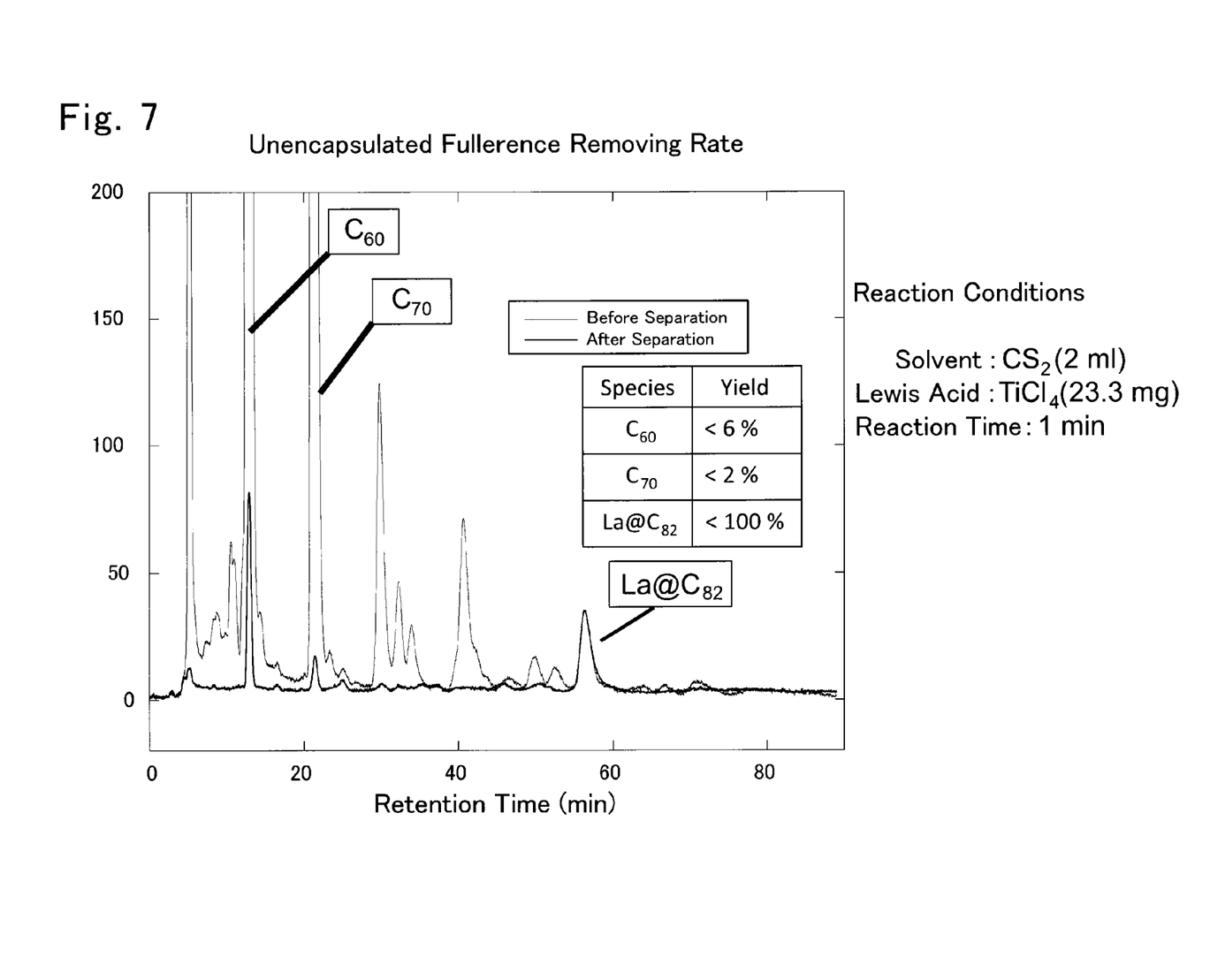
FIG. 7 shows HPLC profiles of fullerenes in a reaction solution before separation and fullerenes in residue after separation in Example 4.

Fullerenes in residue (3) dissolved again in a solvent in the dissolving step was separated by HPLC and an analytical result is shown in FIG. 7. As shown in FIG. 7, in the reaction solution before the complexation step, there were not only an endohedral metallofullerene (La@C82) but also a large amount of unencapsulated fullerenes ($C_{60}$, $C_{70}$). Less than 6 mass % of $C_{60}$, less than 2 mass % of $C_{70}$ and less than 100 mass % of $La@C_{82}$ were detected in the residue obtained by the recovery method when respective amounts of components of fullerenes eluted by HPLC before the complexation step were regarded as 100 mass %. It is clear that most of the unencapsulated fullerenes were separated by the separation of this example.

In Examples 1 to 4 above, the endohedral metallofullerenes which encapsulated any of Gd, Tm, Lu and La were separated. It is clear from this that the method for recovering an endohedral metallofullerene according to the present invention can separate an endohedral metallofullerenes despite the kind of encapsulated metals. It is also clear from Examples 2 and 3 that the method of the present invention can recover a variety of endohedral metallofullerenes at a high recovery yield despite of fullerene size, the number of encapsulated metal element atoms, and valence of a metal element.

Experiment 1

An endohedral metallofullerene (La@C82) was separated by changing conditions of the method for recovering the endohedral metallofullerene. The endohedral metallofullerene was separated by changing a Lewis acid, a solvent, and reaction time used in a complexation step as shown in Conditions 1 to 8. The recovery was carried out in a similar way to that of Example 4, except for using a different Lewis acid, a different solvent and different reaction time. In this example, an encapsulated metal element was La and a Lewis acid was $AlCl_3$, and a solvent was $CS_2$, toluene, o-dichlorobenzene (ODCB) or 1,2,4-trichlorobenzene (TCB) and reaction time was 10 minutes or 24 hours.

A study was conducted on behavior of the endohedral metallofullerene when the endohedral metallofullerene was separated under the respective conditions for separation. Then measured was the ratio of the endohedral metallofullerene left in a filtrate in a filtering step (an unreacted component), the endohedral metallofullerene dissolved again in a solvent in a dissolving step (a recovered component) and the endohedral metallofullerene which was not dissolved in the solvent in the dissolving step and left on a membrane (an insoluble component).

Figure 8:
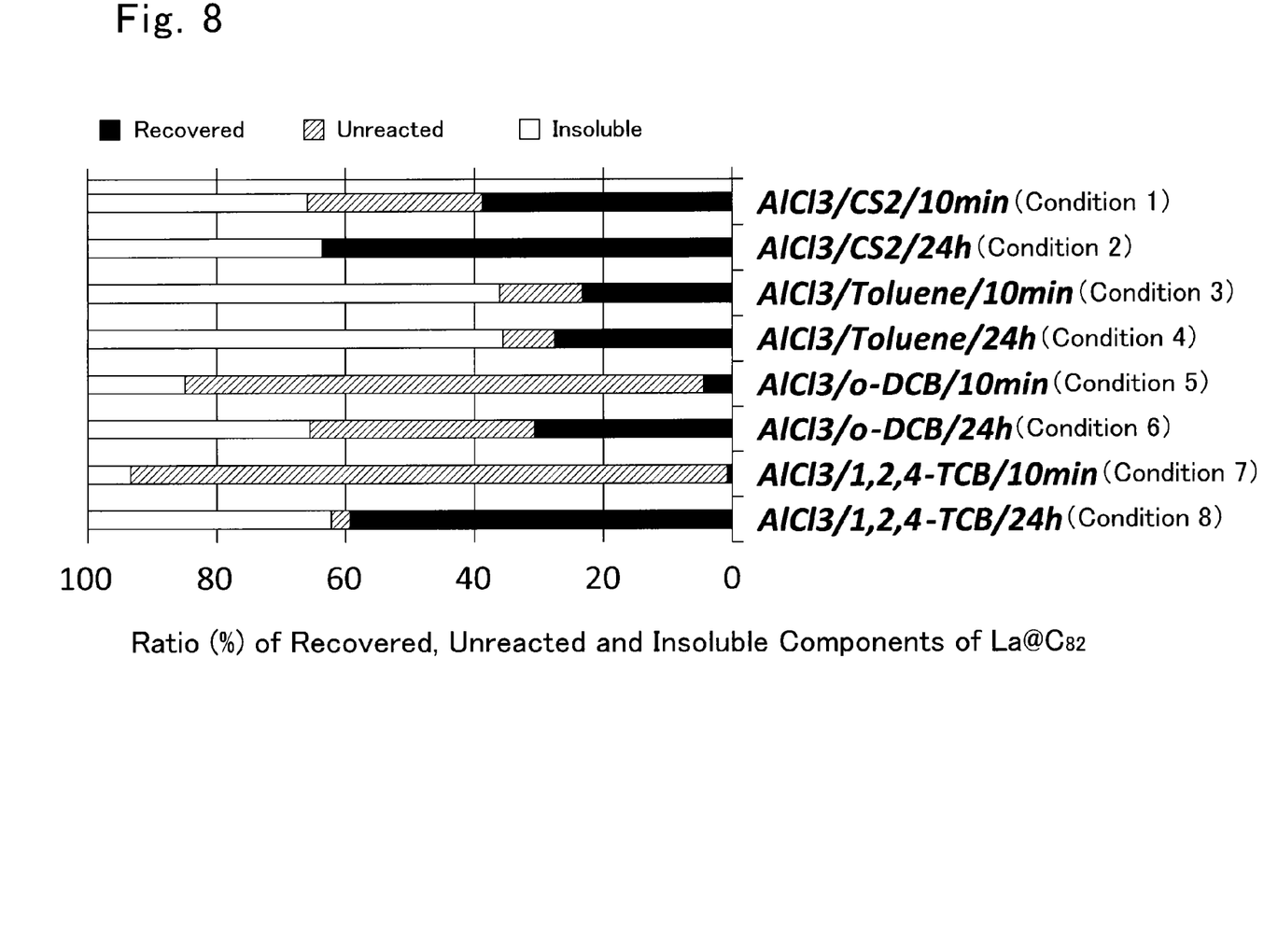
FIG. 8 is a bar graph showing the ratio of an unreacted component, a recovered component, and an insoluble component of an endohedral metallofullerene when the endohedral metallofullerene was separated under Conditions 1 to 8 of Example 1.

In measuring the ratio of the unreacted component, the recovered component and the insoluble component of the endohedral metallofullerene, an La-encapsulated endohedral metallofullerene radioactivated by neutron bombardment was added to a reaction solution as a tracer before separation and intensity of radioactivity derived from La in each of the components was measured, thereby determining the ratio of the unreacted component, the recovered component, and the insoluble component of the endohedral metallofullerene. Of the three components, the recovered component is the endohedral metallofullerene recovered by the recovery method of the present invention. Moreover, the ratio of the recovered component in the total of the unreacted component, the recovered component and the insoluble component is defined as a recovery yield of the endohedral metallofullerene. FIG. 8 shows percentages of the respective components in the total of the unreacted component, the recovered component and the insoluble component when the endohedral metallofullerene was separated under the respective conditions. FIG. 8 also shows the test conditions in the order of Lewis acid/solvent/reaction time. Note that the ratio of respective components and test conditions will be similarly expressed in the drawings after FIG. 8.

As shown in FIG. 8, when $AlCl_3$ was used as a Lewis acid (Conditions 1 to 8), the ratio of the recovered component in the whole endohedral metallofullerene was about 63% or less.

Experiment 2

An endohedral metallofullerene ($La@C_{82}$) was separated under Conditions 9 to 19 in which a Lewis acid and reaction time were changed in a complexation step. A Lewis acid used was $AlBr_3$, $FeCl_3$, $TiCl_4$, or $SnCl_4$, reaction time was 10 minutes or 24 hours, and a solvent used was $CS_2$. The endohedral metallofullerene was separated in a similar way to that of Example 1, except for the above. For comparison, a similar experiment was conducted using $AlF_3$.

The ratio of an unreacted component, a recovered component and an insoluble component of the endohedral metallofullerene was measured in a similar way to that of Example 1. In measuring this ratio, radioactivity was used in the same way as in Example 1 when the endohedral metallofullerene was separated using any one of $AlF_3$, $AlBr_3$, and $FeCl_3$, and a method using HPLC was employed when the endohedral metallofullerene was separated using $TiCl_4$ or $SnCl_4$ as a Lewis acid. In the method using HPLC, amounts of an unrecovered component, a recovered component and an insoluble component of the endohedral metallofullerene were determined from intensity of respective HPLC elution peaks and the ratio of the respective components was calculated from the amounts of the respective components. Use conditions of HPLC were the same as those of Example 1.

Figure 9:
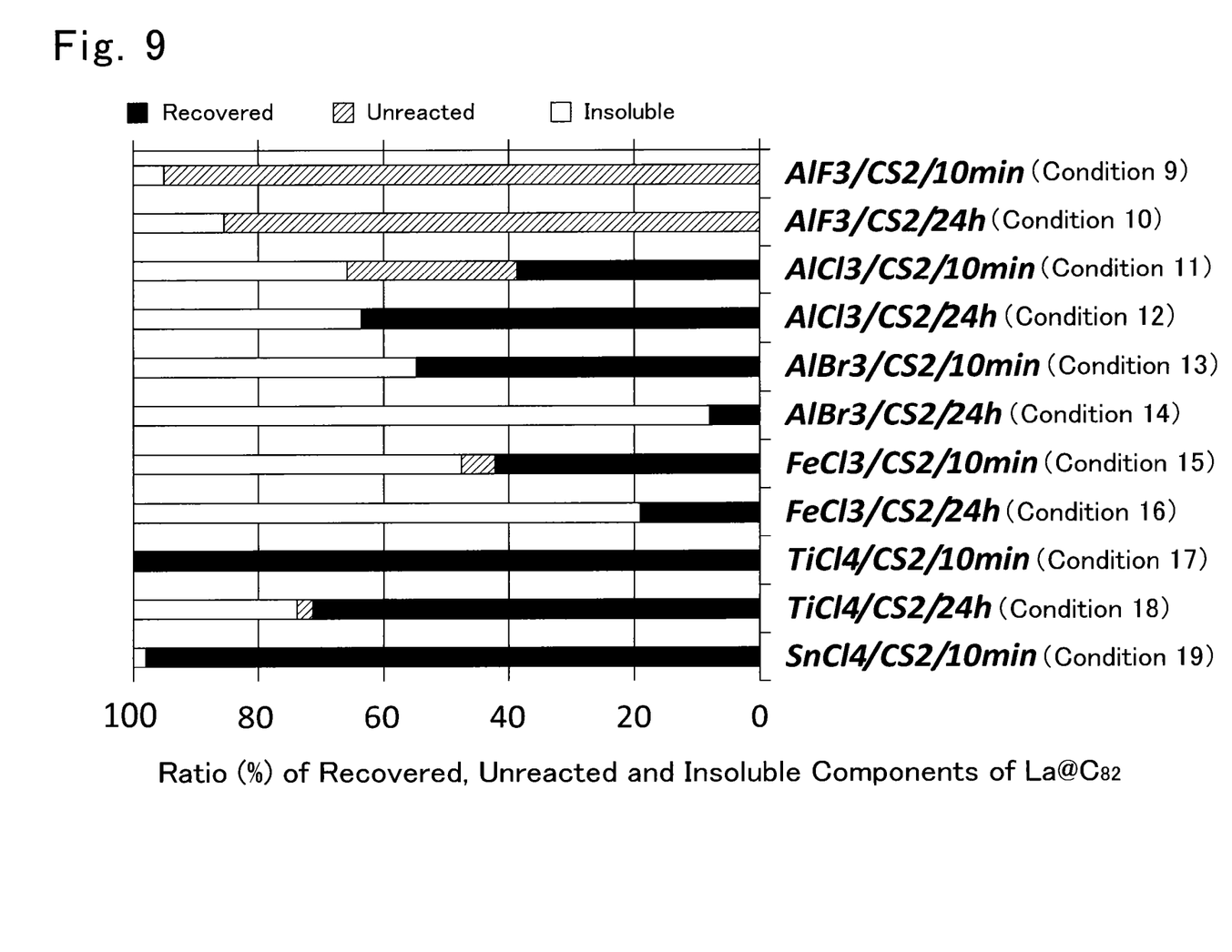
FIG. 9 is a bar graph showing the ratio of an unreacted component, a recovered component, and an insoluble component of an endohedral metallofullerene when the endohedral metallofullerene was separated under Conditions 9 to 19 of Example 2.

As shown in FIG. 9, when the endohedral metallofullerene was separated using $TiCl_4$ or $SnCl_4$ (Conditions 17 to 19), the ratio of the recovered component in the total amount of the endohedral metallofullerene was 70% or more, so the recovery yield was very high. Especially when reaction time was 10 minutes (Conditions 17 and 19), the recovery yield was almost 100%. On the other hand, the endohedral metallofullerene was separated using $AlBr_3$ or $FeCl_3$ (Conditions 11 to 16), the recovery yield was as low as 63% or less. Especially when reaction time was 24 hours (Conditions 14 and 16), the amount of the insoluble component increased and the amount of the recovered component was very small. When $AlF_3$ was used for comparison (Conditions 9 and 10), most of the endohedral metallofullerene was an unreacted component.

It is clear from the above that a halide serving as a Lewis acid is important in separating an endohedral metallofullerene and especially when the endohedral metallofullerene is separated using $TiCl_4$ or $SnCl_4$, the recovery yield of the endohedral metallofullerene is remarkably high.

Experiment 3

An endohedral metallofullerene ($La@C_{82}$) was separated under Conditions 20 to 28 in which a solvent and reaction time were changed in a complexation step. A Lewis acid used was $TiCl_4$. A solvent used was 1,2,4-trichlorobenzene (TCB), $CS_2$, o-xylene or toluene. Reaction time was 1 minute, 5 minutes, 10 minutes, 100 minutes, or 24 hours. The endohedral metallofullerene was separated in a similar way to that of Example 1, except for the above. The ratio of an unreacted component, a recovered component and an insoluble component of the endohedral metallofullerene was determined by HPLC in a similar way to that of Example 1. In measuring this ratio, HPLC was used.

Figure 10:
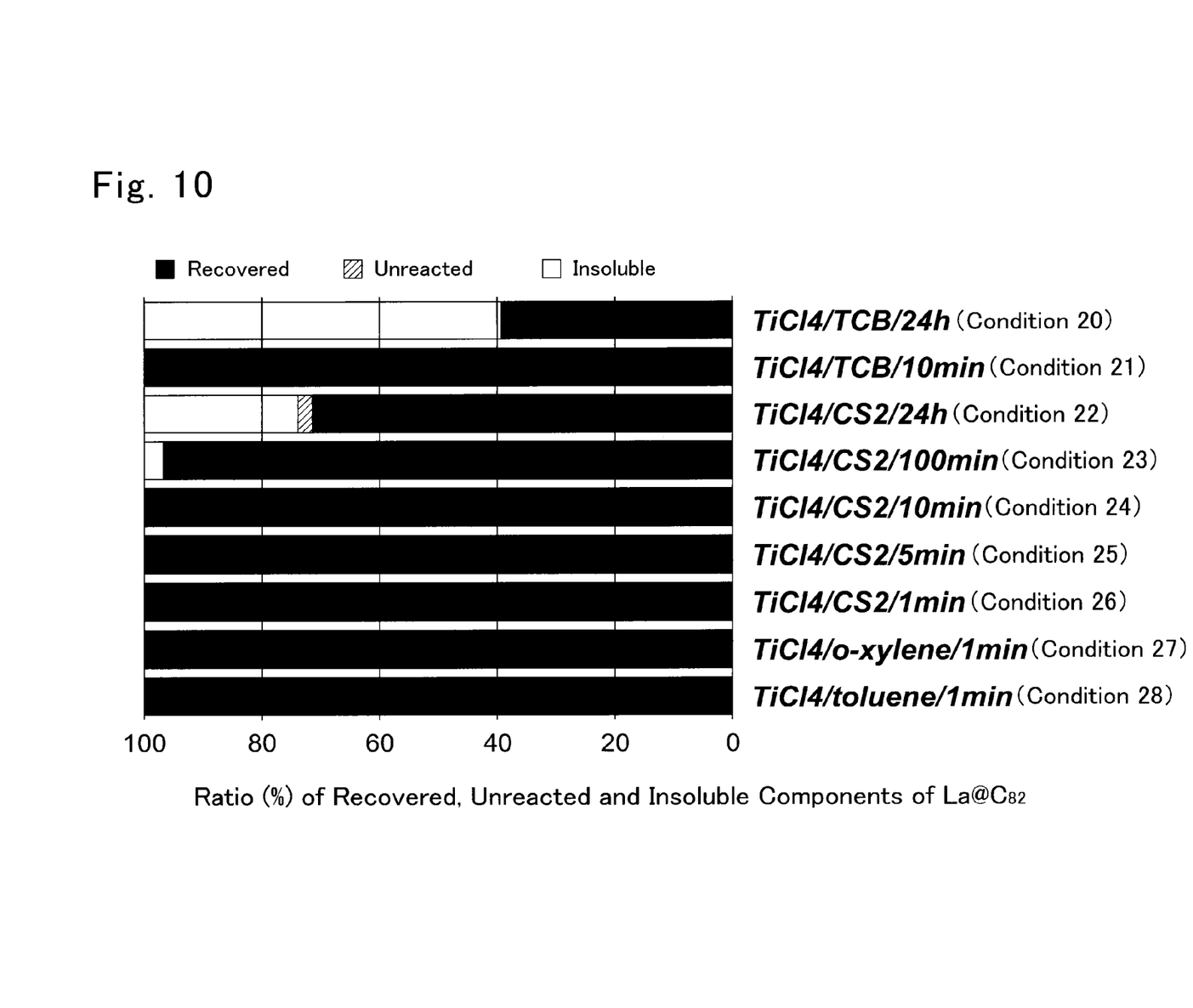
FIG. 10 is a bar graph showing the ratio of an unreacted component, a recovered component, and an insoluble component of an endohedral metallofullerene when the endohedral metallofullerene was separated under Conditions 20 to 28 of Example 3.

As shown in FIG. 10, whichever solvent was used (Conditions 20 to 28), the recovery yield of the endohedral metallofullerene was high. Among them, when reaction time was 10 minutes or less (Conditions 21, 24 to 28), the recovery yield was nearly 100%. On the other hand, when reaction time was 24 hours (Conditions 20, 22), the amount of the insoluble component increased and the recovery yield was low. Especially when TCB was used as a solvent and reaction time was 24 hours (Condition 20), the recovery yield was as low as about 40%. Furthermore, even when a solvent used was $CS_2$ (Conditions 22 to 26), the recovery yield was high when reaction time was 100 minutes or less and the recovery yield was low when reaction time was as long as 24 hours. This demonstrates that as reaction time is shorter, the recovery yield is higher.

Experiment 4

An endohedral metallofullerene ($La@C_{82}$) was separated under Conditions 29 to 31 in which reaction time in a complexation step was changed. A Lewis acid used was $TiCl_4$, a solvent used was $CS_2$, and reaction time was 10, 100 or 1000 minutes. The endohedral metallofullerene was separated in a similar way to that of Example 1, except for the above. The ratio of an unreacted component, a recovered component and an insoluble component of the endohedral metallofullerene was determined using HPLC in a similar way to that of Example 1.

Figure 11:
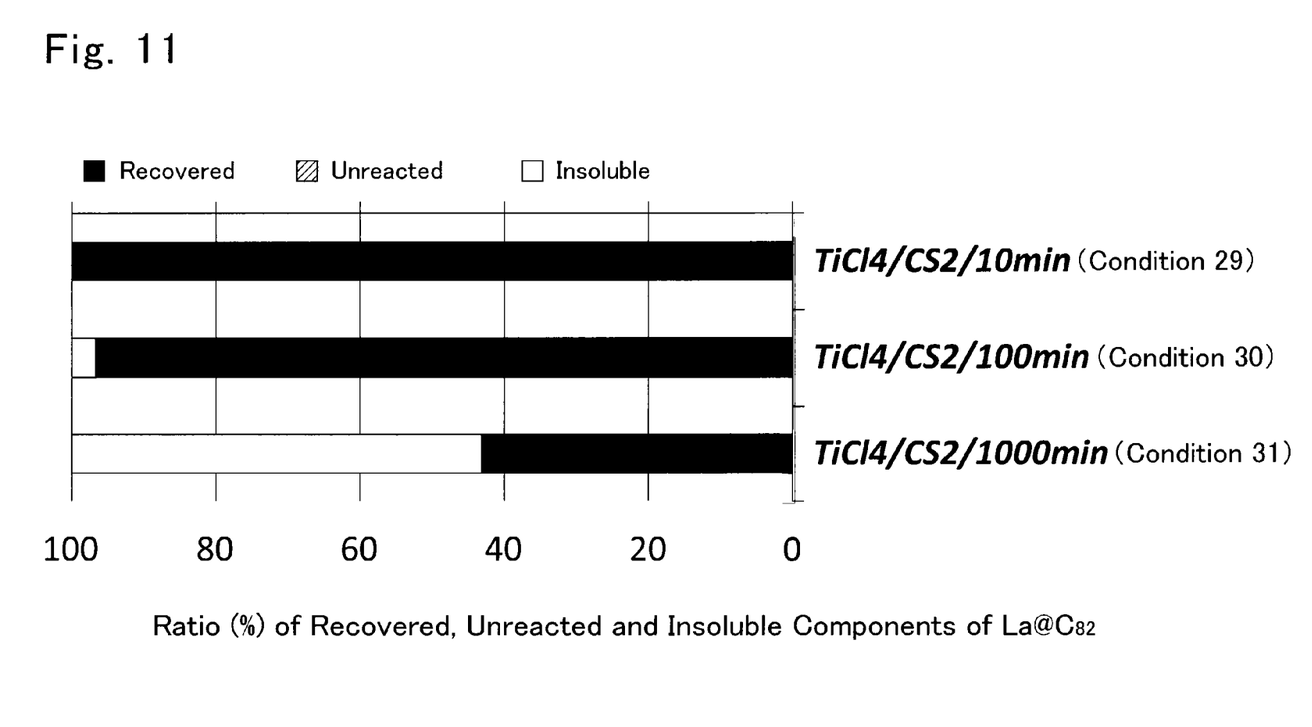
FIG. 11 is a bar graph showing the ratio of an unreacted component, a recovered component, and an insoluble component of an endohedral metallofullerene when the endohedral metallofullerene was separated under Conditions 29 to 31 of Example 4.

As shown in FIG. 11, when reaction time was 100 minutes or less (Conditions 29, 30), the recovery yield of the endohedral metallofullerene was very high, but when reaction time was 1000 minutes (Condition 31), the amount of the insoluble component increased and the recovery yield was considerably low.

The results of Experiments 1 to 4 demonstrate the followings: $TiCl_4$ or $SnCl_4$ is preferred as a Lewis acid used in a method for recovering the endohedral metallofullerene. A solvent only has to dissolve fullerenes and, for example, $CS_2$ and benzene-based solvents are preferred. Shorter reaction time is better and, if circumstances permit, 100 minutes or less or 10 minutes or less is preferred. Reason why the recovery yield of the endohedral metallofullerene decreases with increase reaction time is assumed to be that the endohedral metallofullerene is polymerized by a Lewis acid, so the amount of an insoluble component increases.

In this example, almost 100% of the endohedral fullerene was recovered by forming a complex of the endohedral metallofullerene and $TiCl_4$ by adding $TiCl_4$ as a Lewis acid, and filtering this to obtain residue, washing the residue with water, and then passing the residue through $CS_2$, benzene-based solvents or the like. Time necessary for separation, i.e., the total of the complexation step, the filtering step, the washing step and the dissolving step was about 20 minutes.

The invention claimed is:

1. A method for recovering an endohedral metallofullerene from crude fullerenes, comprising:
    adding a Lewis acid comprising at least one of titanium halide and tin halide to a reaction solution formed by dissolving the crude fullerenes in a solvent, thereby forming a solution comprising a complex of the endohedral metallofullerene and the Lewis acid;
    filtering the solution comprising the complex of the endohedral metallofullerene and the Lewis acid to separate the complex; and
    removing the Lewis acid from the separated complex by washing said complex to obtain the endohedral metallofullerene,
    wherein a reaction time of the endohedral metallofullerene and the Lewis acid is not less than 0.2 seconds and less than 1 hour.

2. The method for recovering the endohedral metallofullerene according to claim 1, wherein the Lewis acid comprises at least one of titanium chloride and tin chloride.

3. The method for recovering the endohedral metallofullerene according to claim 1, wherein the solvent is at least one selected from the group consisting of $CS_2$ and benzene-based solvents.

4. The method for recovering the endohedral metallofullerene according to claim 1, wherein the complex is constituted by one molecule of the endohedral metallofullerene and a plurality of molecules of the Lewis acid.

5. The method for recovering the endohedral metallofullerene according to claim 1, wherein the Lewis acid is removed by washing the complex with water.

6. The method for recovering the endohedral metallofullerene according to claim 1, wherein the crude fullerenes include the endohedral metallofullerene and an unencapsulated fullerene which encapsulates no metal.

7. The method for recovering the endohedral metallofullerene according to claim 1, further comprising dissolving the endohedral metallofullerene in a second solvent after the washing.

8. The method for recovering the endohedral metallofullerene according to claim 7, wherein the second solvent is at least one selected from the group consisting of $CS_2$ and benzene-based solvents.

9. The method for recovering the endohedral metallofullerene according to claim 7, wherein the second solvent is different from the solvent in the reaction solution.

10. A method for recovering an endohedral metallofullerene from crude fullerenes, comprising:
    adding a Lewis acid comprising at least one of titanium halide and tin halide to a reaction solution formed by dissolving the crude fullerenes in a solvent, thereby forming a solution comprising a complex of the endohedral metallofullerene and the Lewis acid;

filtering the solution comprising the complex of the endohedral metallofullerene and the Lewis acid to separate the complex; and removing the Lewis acid from the separated complex by washing said complex to obtain the endohedral metallofullerene, wherein the crude fullerenes are extracted from soot generated by applying wheat treatment to a composite rod of carbon and a metal wherein a reaction time of the endohedral metallofullerene and the Lewis acid is not less than 0.2 seconds and less than 1 hour.

11. The method for recovering the endohedral metallofullerene according to claim 10, wherein the Lewis acid comprises at least one of titanium chloride and tin chloride.

12. The method for recovering the endohedral metallofullerene according to claim 10, wherein the solvent is at least one selected from the group consisting of $CS_2$ and benzene-based solvents.

13. The method for recovering the endohedral metallofullerene according to claim 10, wherein the complex is constituted by one molecule of the endohedral metallofullerene and a plurality of molecules of the Lewis acid.

14. The method for recovering the endohedral metallofullerene according to claim 10, wherein the Lewis acid is removed by washing the complex with water.

15. The method for recovering the endohedral metallofullerene according to claim 10, wherein the crude fullerenes include the endohedral metallofullerene and an unencapsulated fullerene which encapsulates no metal.

16. The method for recovering the endohedral metallofullerene according to claim 10, further comprising dissolving the endohedral metallofullerene in a second solvent after the washing.

17. The method for recovering the endohedral metallofullerene according to claim 16, wherein the second solvent is at least one selected from the group consisting of $CS_2$ and benzene-based solvents.

18. The method for recovering the endohedral metallofullerene according to claim 16, wherein the second solvent is different from the solvent in the reaction solution.

* * * * *